United States Patent
Lee et al.

(10) Patent No.: US 6,453,489 B1
(45) Date of Patent: Sep. 24, 2002

(54) FAUCET COUPLING DEVICE FOR COUPLING TO VARIOUS MEMBERS

(76) Inventors: Terng Yaw Lee, No. 134, Din Lie Road, Sien Hsi Hsiang, Chang Hua Hsien (TW), 507; Hung Mao Lee, No. 522, Sec. 2, Chang Nan Road, Chang Hua (TW), 500

( * ) Notice: Subject to any disclaimer, the term of this patent is extended or adjusted under 35 U.S.C. 154(b) by 0 days.

(21) Appl. No.: 09/839,094

(22) Filed: Apr. 23, 2001

(51) Int. Cl.[7] ............................................. E03C 1/04
(52) U.S. Cl. ............................. 4/675; 4/448; 604/150
(58) Field of Search ........................... 4/675, 676, 677, 4/678, 448, 443; 239/583, 586, 304, 305; 401/278–282; 137/843; 285/8; 604/150

(56) References Cited

U.S. PATENT DOCUMENTS

| | | | | |
|---|---|---|---|---|
| 1,682,470 A | * | 8/1928 | Bassett | 401/43 |
| 2,829,645 A | * | 4/1958 | Matteson | 604/150 |
| 3,055,392 A | * | 9/1962 | Barotz | 137/562 |
| 3,254,647 A | * | 6/1966 | Vogel | 604/85 |
| 3,273,189 A | * | 9/1966 | Levinson et al. | 4/443 |
| 3,485,454 A | * | 12/1969 | Walker | 239/434 |
| 3,500,824 A | * | 3/1970 | Gilbert | 601/165 |
| 3,593,707 A | * | 7/1971 | Pifer | 128/66 |
| 3,682,176 A | * | 8/1972 | Kelsen | 128/229 |
| 4,287,618 A | * | 9/1981 | Silver | 4/443 |
| 5,876,135 A | | 3/1999 | Wang et al. | 401/46 |
| 5,937,451 A | * | 8/1999 | Mihara | 4/448 |

* cited by examiner

Primary Examiner—David J. Walczak
Assistant Examiner—Huyen Le
(74) Attorney, Agent, or Firm—Charles E. Baxley

(57) ABSTRACT

A faucet coupling device includes a housing secured to a faucet and having a channel and a port and an aperture and an outlet opening communicating with each other. A nozzle is coupled to the aperture of the housing, and one or more cleaning members may be selectively coupled to the port. A switch device is disposed in the channel of the housing for switching between the outlet opening and the aperture and the port of the housing, and for controlling the water to flow through the outlet opening of the housing or the nozzle or the cleaning members.

16 Claims, 5 Drawing Sheets

FAUCET COUPLING DEVICE FOR COUPLING TO VARIOUS MEMBERS

BACKGROUND OF THE INVENTION

1. Field of the Invention

The present invention relates to a faucet, and more particularly to a faucet coupling device for coupling various cleaning members to the faucet.

2. Description of the Prior Art

U.S. Pat. No. 5,876,135 to Wang et al. discloses a typical faucet coupling device attached to the faucet for coupling the faucet to a brush cleaning member. However, faucet coupling device and the cleaning members may not be easily used to rinse the mouth or the like.

The present invention has arisen to mitigate and/or obviate the afore-described disadvantages of the conventional faucet coupling devices.

SUMMARY OF THE INVENTION

The primary objective of the present invention is to provide a faucet coupling device for coupling various cleaning members to the faucet and for easily rinsing the mouth.

In accordance with one aspect of the invention, there is provided a faucet coupling device for a faucet, the faucet coupling device comprising a housing for attaching to the faucet and for receiving water from the faucet, the housing including a channel formed therein, and including a port and an aperture and an outlet opening formed therein and communicating with the channel thereof, a nozzle coupled to the aperture of the housing, a cleaning member coupled to the port of the housing, and means for switching between the outlet opening and the aperture and the port of the housing, to control the water to flow through the outlet opening of the housing and the nozzle and the cleaning member.

A hose is further provided and includes a first end coupled to the port of the housing and includes a second end coupled to the cleaning member.

A device is further provided for coupling the second end of the hose to the cleaning member and includes a coupler coupled between the second end of the hose and the cleaning member, the coupler includes a bore formed therein and communicating the hose with the cleaning member, and includes means for detachably securing the cleaning member to the coupler.

The cleaning member includes a pipe, the detachably securing means includes a barrel secured to the coupler for receiving the pipe, at least one ball received in the barrel and extendible inward of the barrel to engage with and the secure the pipe to the barrel and the coupler.

The detachably securing means includes a control ferrule slidably engaged on the barrel and having a peripheral bulge extended inward therefrom for engaging with the ball and for forcing the ball to engage with the pipe.

A spring biasing device is further provided for biasing the peripheral bulge of the control ferrule to engage with the ball.

The coupler includes a chamber formed therein and communicating with the bore of the coupler, a block slidably received in the chamber of the coupler and having a groove formed therein for aligning with the bore of the coupler, and means for biasing and disengaging the groove of the block from the bore of the coupler.

The block includes a knob extended outward of the coupler, the biasing means includes a spring engaged with the block for biasing the knob outward of the coupler.

A device is further provided for paddling the water through the port and the aperture of the housing and includes a valve casing secured in the channel of the housing and having an end wall, a paddle wheel rotatably secured to the end wall.

The valve casing includes a bore formed therein, the end wall of the valve casing includes a notch formed therein and communicating with the bore of the valve casing for allowing the paddle wheel to paddle the water through the bore of the valve casing.

The switching means includes a valve member secured in the channel of the housing, the housing includes an inlet communicating with the channel of the housing, the valve member includes a first valve seat provided between the channel and the outlet opening of the housing, and includes a second valve seat provided between the inlet and the port and the aperture of the housing, and means for selectively engaging with the first and the second valve seats.

The selectively engaging means includes a valve stem slidably engaged in the valve member and having two plugs secured thereto for selectively engaging with the first and the second valve seats.

A conduit is further provided and secured to the aperture of the housing and communicating with the channel of the housing, a duct slidably engaged in the conduit and including an outer end extended outward of the conduit for securing to the nozzle.

The conduit includes a valve seat provided therein, the duct includes an inner end slidably received in the conduit and having a head for engaging with the valve seat of the conduit, and means for biasing the head to engage with and to block the valve seat of the conduit so as to block the water and to prevent the water from flowing out through the nozzle.

The duct includes a bore formed therein, and includes at least one orifice formed therein for communicating the bore of the duct with the conduit and for allowing the water from the conduit to flow through the orifice of the duct into the bore of the duct.

Further objectives and advantages of the present invention will become apparent from a careful reading of a detailed description provided hereinbelow, with appropriate reference to accompanying drawings.

DETAILED DESCRIPTION OF THE PREFERRED EMBODIMENT

Figure 1:
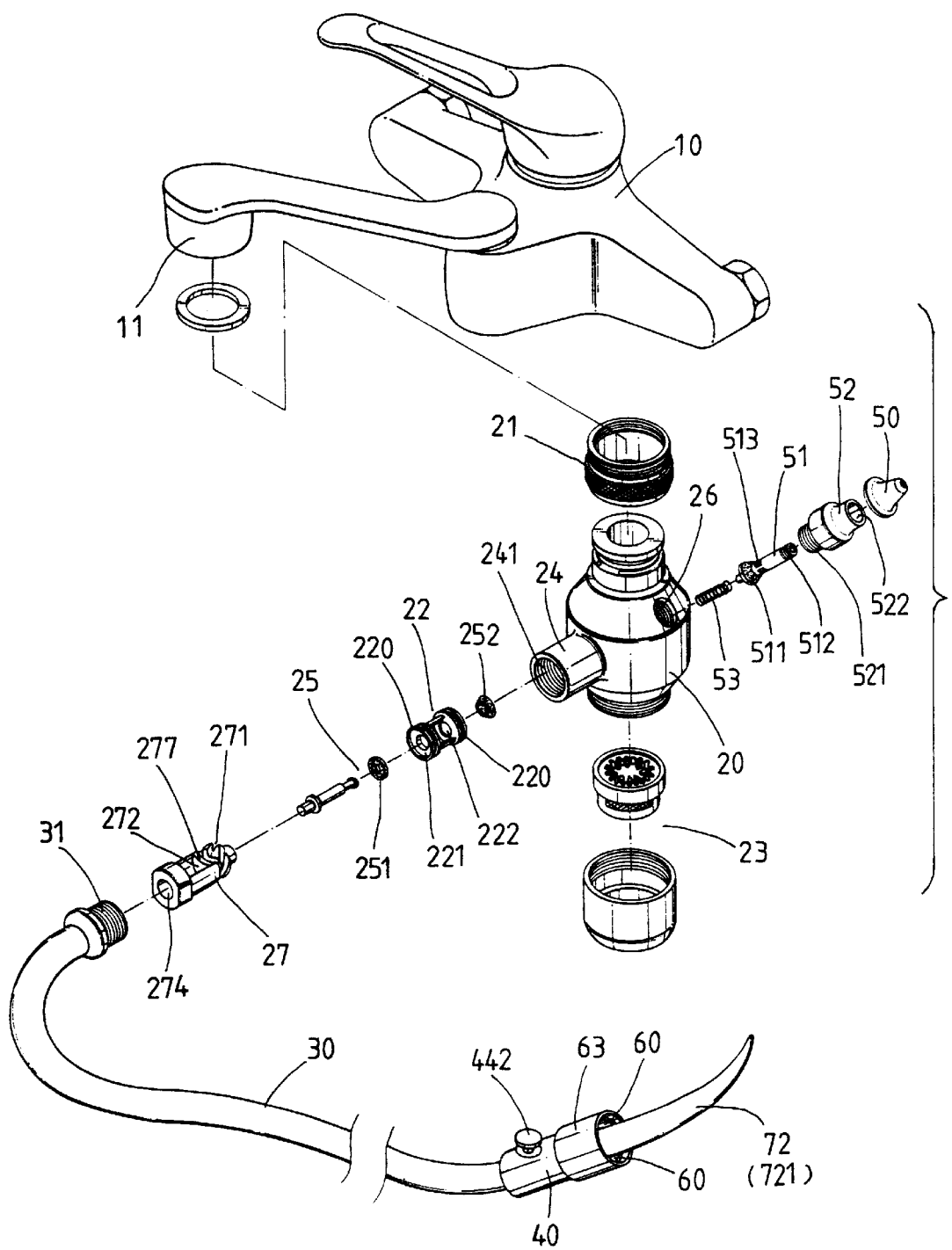
FIGS. 1 and 2 are partial exploded views of a faucet coupling device in accordance with the present invention.

Referring to the drawings, and initially to FIGS. 1–4, a faucet coupling device in accordance with the present invention comprises a housing 20 secured or attached to an outlet 11 of a faucet 10 or the like. The housing 20 may be directly threaded and secured to the outlet 11 of the faucet 10 (FIGS. 3–5), or may be rotatably secured to a cylindrical member 21 which may then be used for threading and securing to the outlet 11 of the faucet 10 (FIG. 1). The housing 20 includes a outlet opening 201 formed and provided in the bottom portion thereof for discharging the water, and includes a port 24 laterally extended outward therefrom and having an inner thread 241 formed therein. A water pacifier 23 or the like may be attached to the bottom of the housing 20 and communicating with the outlet opening 201 of the housing 20 for allowing the water to flow out through the water pacifier 23.

The housing 20 includes a middle portion having a channel 202 laterally formed therein and formed in the port 24, and includes a passage 203 formed between the channel 202 and the outlet opening 201 thereof for allowing the water to flow out through the outlet opening 201, and includes a passageway 204 formed between the channel 202 and the upper inlet 207 thereof for allowing the water to flow into the channel 202 of the housing 20. A valve member 22 is secured in the housing 20 and disposed between the channel 202 and the passage 203 and the passageway 204 of the housing 20, and includes two end plates 220 each having a valve seat 221, 222 provided therein, in which the valve seat 221 is facing toward the port 24 and provided between the inlet 207 and the port 24 of the housing 20, and the other valve seat 222 is provided between the inlet 207 and the passage 203 of the housing 20. A valve stem 25 is slidably engaged in the valve member 22. Two plugs 251, 252 are secured to the ends of the valve stem 25 for engaging with either of the valve seats 221, 222 of the valve member 22.

A valve casing 27 is received in the port 24, and includes an inner end wall 272 located close to the valve member 22, and includes a bore 274 formed therein. The inner end wall 272 includes a notch 277 formed therein for communicating the bore 274 of the valve casing 27 with the channel 202 of the housing 20. A paddle wheel 271 is secured to the end wall 272 of the valve casing 27 with fasteners 273 or the like, such that the water from the channel 202 of the housing 20 should flow through the paddle wheel 271 before flowing into the bore 274 of the valve casing 27. A hose 30 includes a threaded coupler 31 provided on one end thereof for threading or coupling to the inner thread 241 of the port 24. The coupler 31 may be used for retaining the valve casing 27 within the port 24 of the housing 20.

A coupler 40 includes a threaded extension 42 for threading and securing to the other end of the hose 30, and includes a bore 41 formed therein and communicating with the hose 30, and includes a chamber 43 formed therein and intersecting or communicating with the bore 41 thereof. A block 44 is slidably received in the inner portion or in the chamber 43 of the coupler 40, and includes a groove 441 formed therein for selectively aligning with the bore 41 of the coupler 40 (FIG. 5), and includes a knob 442 attached to a rod 443 which is extended outward through a cap or a stop 45 of the coupler 40. A spring 46 is received in the chamber 43 of the coupler 40 and engaged with the block 44 for disengaging the groove 441 of the block 44 from the bore 41 of the coupler 40 (FIG. 3), and for biasing the knob 442 outward of the coupler 40. One or more sealing rings 47 may be disposed between the block 44 and the coupler 40 for making a water tight seal between the block 44 and the coupler 40.

A barrel 60 is threaded or secured to the outer end of the coupler 40. A control ferrule 63 is rotatably engaged onto the barrel 60, and includes a peripheral bulge 67 extended inward therefrom. One or more rollers or balls 61 or the like are engaged in the barrel 60 and partially extended inward of the barrel 60. A clamping ring 64 may be engaged onto the outer portion of the barrel 60 for retaining the balls 61 between the barrel 60 the control ferrule 63, and for preventing the balls 61 from being disengaged from the barrel 60. A spring 62 is engaged between the barrel 60 and the control ferrule 63 for biasing and forcing the peripheral bulge 67 of the control ferrule 63 to engage with and to force the balls 61 inward of the barrel 60.

One or more cleaning members 72, such as the ejecting nozzle 721, the tooth brush device 722, the shower head 723, etc., each includes a pipe 70 extended outward therefrom, and each includes a peripheral depression 71 formed on the outer peripheral portion of the pipe 70 for receiving the balls 61 and for detachably securing to the coupler 40. The balls 61 may be forced inward of the barrel 60 and engaged into the peripheral depression 71 of the cleaning members 72 by the spring-biased peripheral bulge 67 of the control ferrule 63, in order to detachably secure the cleaning members 72 to the coupler 40. The balls 61 may be disengaged from the peripheral depressions 71 of the pipes 70 when the control ferrule 63 is moved relative to the barrel 60 against the spring 62.

Figure 3:
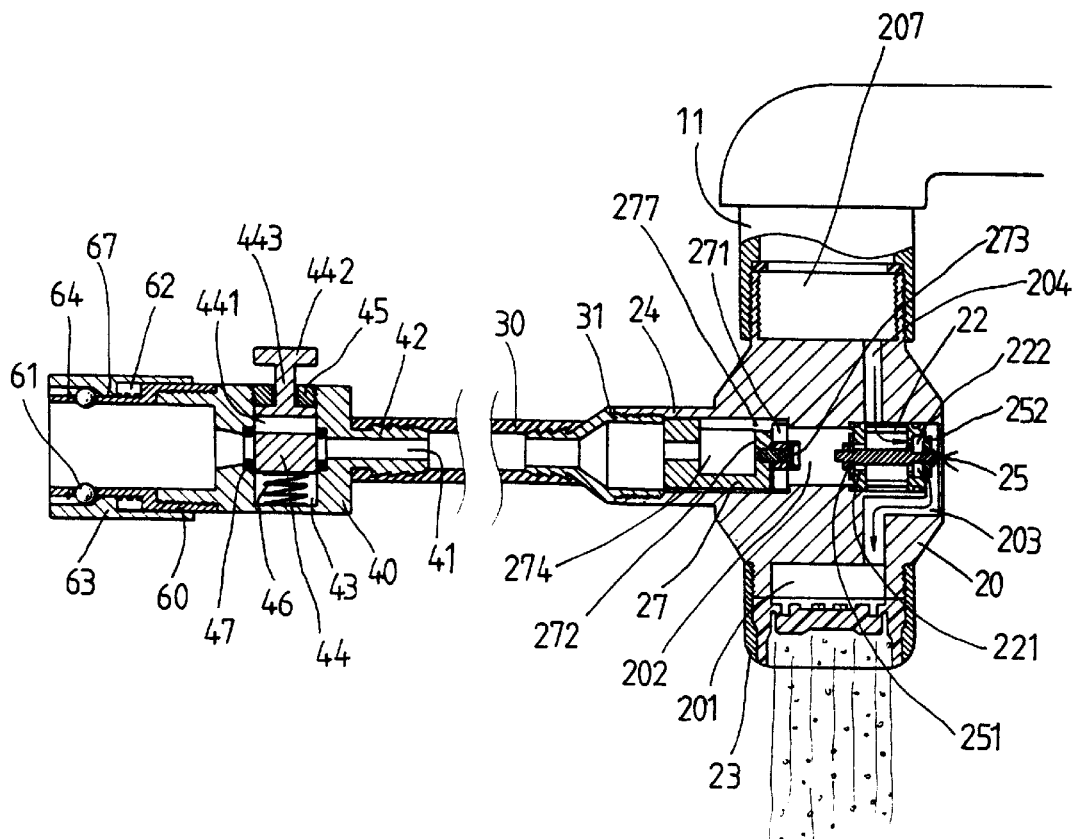
FIGS. 3 and 4 are partial cross sectional views taken along lines 3—3 and 4—4 of FIG. 2 respectively.
Figure 5:
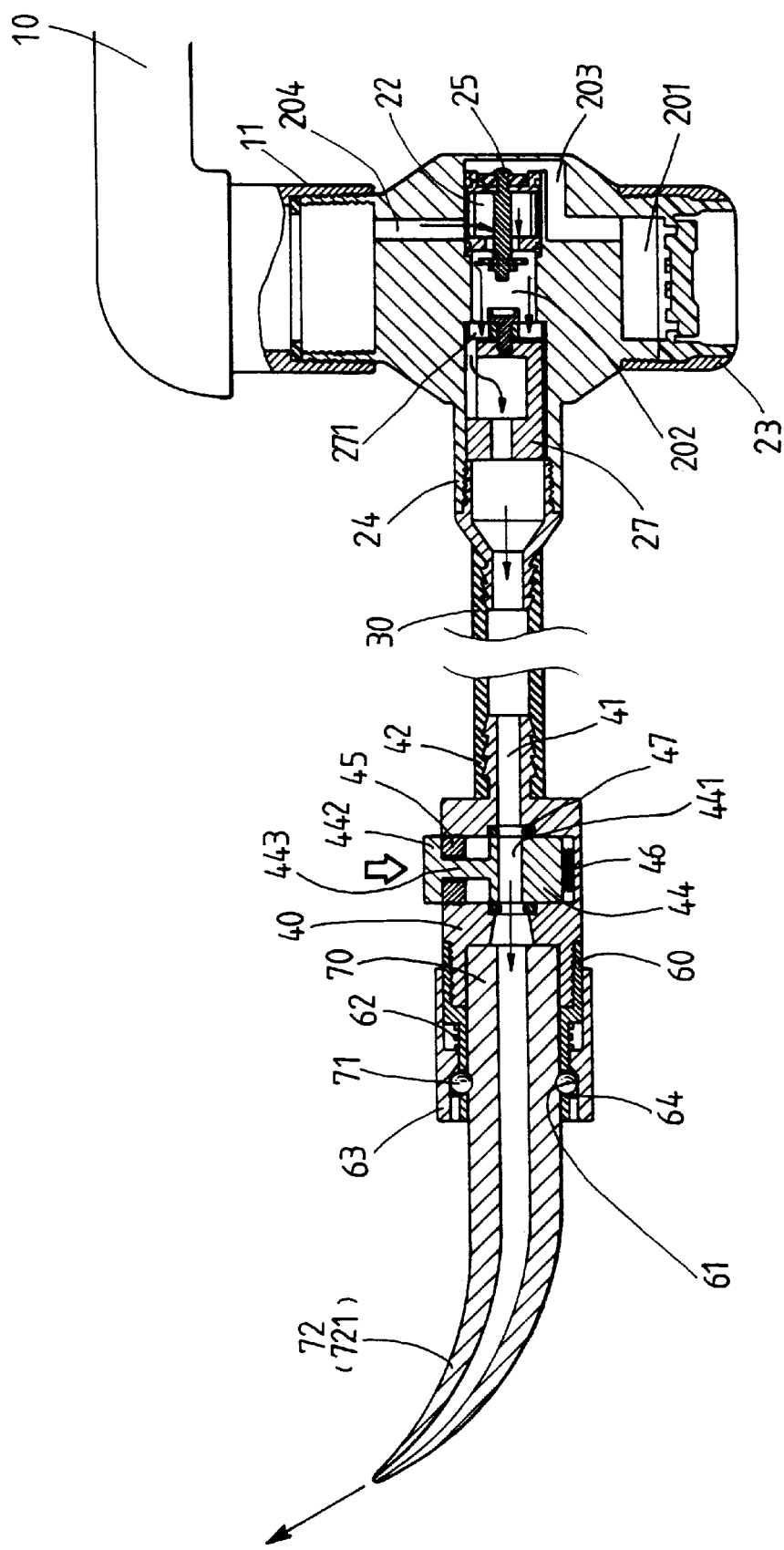
FIGS. 5, 6, 7 are partial cross sectional views similar to FIG. 3, illustrating the operation of the faucet coupling device.
Figure 6:
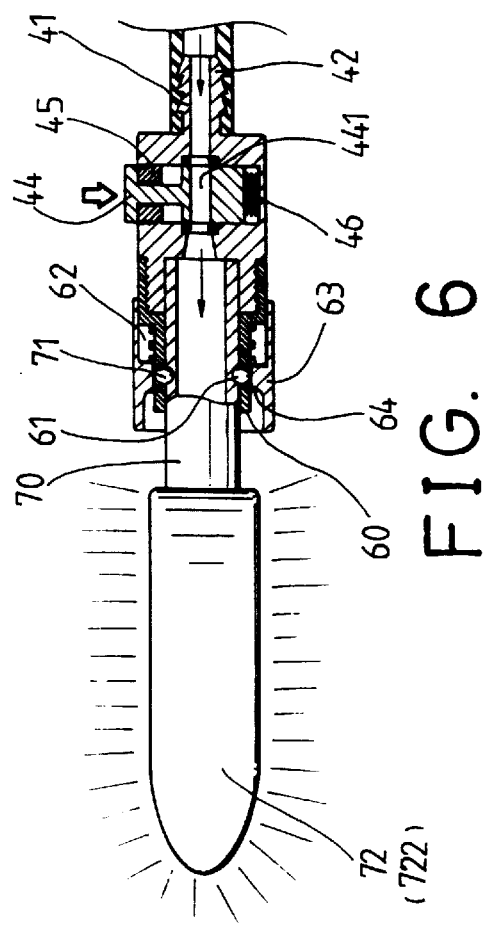
Figure 7:
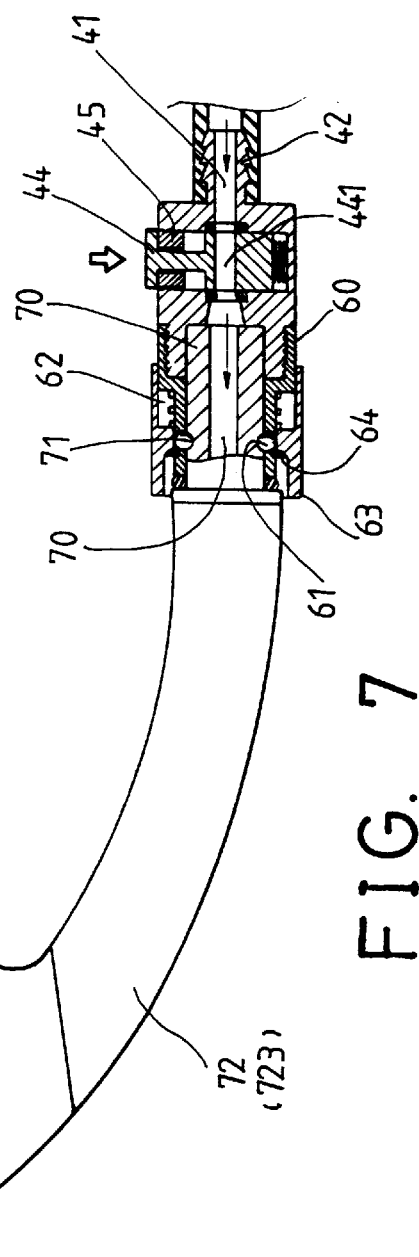

In operation, as shown in FIG. 3, when the groove 441 of the block 44 is biased and disengaged from the bore 41 of the coupler 40 by the spring 46, the water may not flow through the block 44. When the faucet is opened, the water from the inlet 207 of the housing 20 may force and disengage the plug 252 from the valve seat 222 of the valve member 22 and may only flow out through the outlet opening 201 of the housing 20 via the passage 203 of the housing 20. As shown in FIG. 5, when the block 44 is depressed against the spring 46 by the knob 442 to align the groove 441 of the block 44 with bore 41 of the coupler 40, the pressure in the hose 30 is released, and the water from the inlet 207 of the housing 20 may force and disengage the plug 251 from the valve seat 221 of the valve member 22 and may thus flow out through either of the cleaning members 72 via the paddle wheel 271 and the valve casing 27, in order to spray and to clean the teeth with the ejecting nozzle 721 (FIG. 5), or to brush the teeth with the tooth brush device 722 (FIG. 6), or to shower with the shower head 723 (FIG. 7). At this moment, the plug 252 is arranged to be engaged with the valve seat 222 of the valve member 22 to prevent and to block the water from flowing through the passage 203 and the outlet opening 201 of the housing 20.

Figure 2:
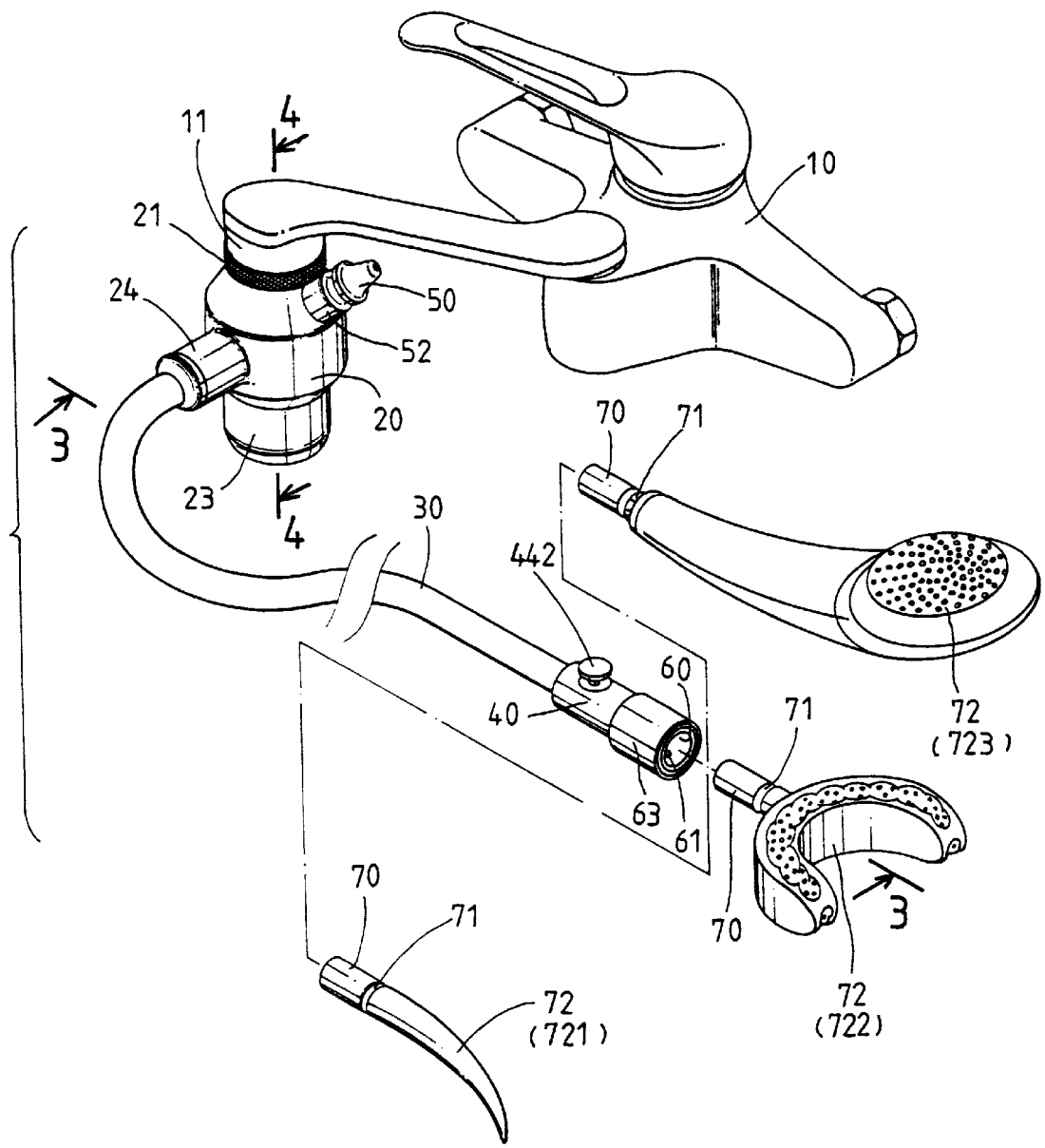
Figure 4:
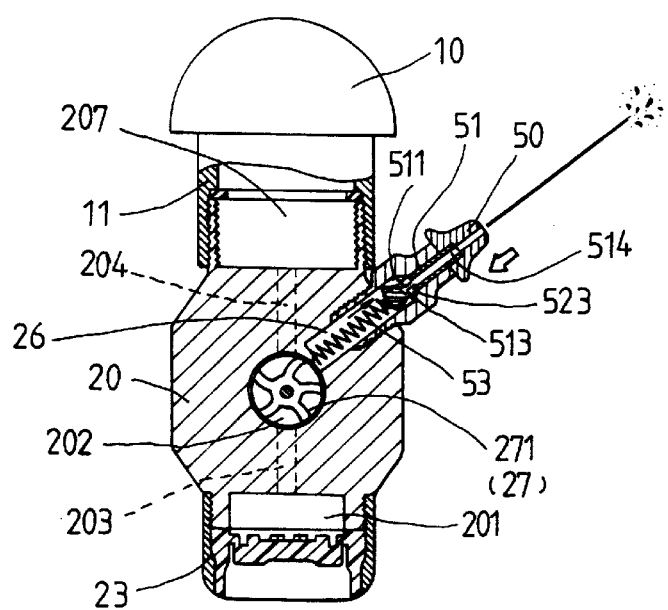

As shown in FIGS. 1, 2, and 4, the housing 20 further includes a threaded aperture 26 formed in the upper portion thereof and facing partially sidewise and partially upward, and communicating with the channel 202 of the housing 20, and preferably aligned with the paddle wheel 271 (FIG. 4), for allowing the water from the channel 202 of the housing 20 and from the paddle wheel 271 to flow out through the aperture 26 of the housing 20. A conduit 52 includes an outer thread 521 formed on one end thereof for threading and securing to the threaded aperture 26 of the housing 20, and includes a bore 522 formed therein and communicating with the aperture 26 of the housing 20, and includes a valve seat 523 (FIG. 4) formed and provided in the inner portion thereof.

A duct 51 is slidably engaged in the bore 522 of the conduit 52, and includes a threaded outer end 512 (FIG. 1) for threading and securing to a nozzle 50, and includes an enlarged head 511 formed and provided in the inner end thereof for engaging with the valve seat 523 of the conduit 52, and includes one or more orifices 513 formed therethrough and communicating with the bore 514 of the duct 51 and with the bore 522 of the conduit 52, for allowing the water in the aperture 26 of the housing 20 to flow out through the nozzle 50 via the bore 522 of the conduit 52 and the orifices 513 and the bore 514 of the duct 51. A spring 53 is engaged with the head 511 of the duct 51 for biasing the head 511 to engage with the valve seat 523 of the conduit 52 and to block the water.

In operation, as shown in FIGS. 4, 5, when the head 511 of the duct 51 is depressed against the spring 53 and disengaged from the valve seat 523 of the conduit 52 by depressing the nozzle 50, the pressure in the hose 30 may also be released, and the water from the inlet 207 of the housing 20 may force and disengage the plug 251 from the valve seat 221 of the valve member 22 and may thus flow out through the nozzle 50 via the paddle wheel 271 and the valve casing 27. At this moment, the plug 252 is arranged to be engaged with the valve seat 222 of the valve member 22 to prevent and to block the water from flowing through the passage 203 and the outlet opening 201 of the housing 20. When the nozzle 50 is released, the spring 53 may bias the head 511 to engage with the valve seat 523 of the conduit 52 again and to block the water again. At this moment, the water may only flow out through the outlet opening 201 of the housing 20. The water flowing out of the nozzle 50 may be used for rinsing the teeth or the mouth, or the like.

It is to be noted that the provision of the spring-biased nozzle 50 allows the users to easily rinse their teeth or mouth, without using the cleaning members 72, and without changing and coupling the cleaning members 72 to the coupler 40.

Accordingly, the faucet coupling device in accordance with the present invention may be used for coupling various cleaning members to the faucet and may be used for easily rinsing the mouth.

Although this invention has been described with a certain degree of particularity, it is to be understood that the present disclosure has been made by way of example only and that numerous changes in the detailed construction and the combination and arrangement of parts may be resorted to without departing from the spirit and scope of the invention as hereinafter claimed.

We claim:

1. A faucet coupling device for a faucet, said faucet coupling device comprising:
   a) a housing for attaching to the faucet and for receiving water from the faucet, said housing including a channel formed therein, and including a port and an aperture and an outlet opening formed therein and communicating with said channel thereof,
   b) a nozzle coupled to said aperture of said housing,
   c) a cleaning member coupled to said port of said housing,
   d) means for switching between said outlet opening and said aperture and said port of said housing, to control the water to flow through said outlet opening of said housing and said nozzle and said cleaning member, and
   e) means for paddling the water through said port and said aperture of said housing.

2. The faucet coupling device according to claim 1 further comprising a hose including a first end coupled to said port of said housing and including a second end coupled to said cleaning member.

3. The faucet coupling device according to claim 2 further comprising means for coupling said second end of said hose to said cleaning member.

4. The faucet coupling device according to claim 3, wherein said coupling means includes a coupler coupled between said second end of said hose and said cleaning member, said coupler includes a bore formed therein and communicating said hose with said cleaning member, and includes means for detachably securing said cleaning member to said coupler.

5. The faucet coupling device according to claim 4, wherein said cleaning member includes a pipe, said detachably securing means includes a barrel secured to said coupler for receiving said pipe, at least one ball received in said barrel and extendible inward of said barrel to engage with and said secure said pipe to said barrel and said coupler.

6. The faucet coupling device according to claim 5, wherein said detachably securing means includes a control ferrule slidably engaged on said barrel and having a peripheral bulge extended inward therefrom for engaging with said at least one ball and for forcing said at least one ball to engage with said pipe.

7. The faucet coupling device according to claim 6 further comprising means for biasing said peripheral bulge of said control ferrule to engage with said at least one ball.

8. The faucet coupling device according to claim 4, wherein said coupler includes a chamber formed therein and communicating with said bore of said coupler, a block slidably received in said chamber of said coupler and having a groove formed therein for aligning with said bore of said coupler, and means for biasing and disengaging said groove of said block from said bore of said coupler.

9. The faucet coupling device according to claim 8, wherein said block includes a knob extended outward of said coupler, said biasing means includes a spring engaged with said block for biasing said knob outward of said coupler.

10. The faucet coupling device according to claim 1, wherein said paddling means includes a valve casing secured in said channel of said housing and having an end wall, a paddle wheel rotatably secured to said end wall.

11. The faucet coupling device according to claim 10, wherein said valve casing includes a bore formed therein, said end wall of said valve casing includes a notch formed therein and communicating with said bore of said valve casing for allowing said paddle wheel to paddle the water through said bore of said valve casing.

12. A faucet coupling device for a faucet, said faucet coupling device comprising:
   a) a housing for attaching to the faucet and for receiving water from the faucet, said housing including a channel formed therein, and including a port and an aperture and an outlet opening formed therein and communicating with said channel thereof,
   b) a nozzle coupled to said aperture of said housing,
   c) a cleaning member coupled to said port of said housing, and
   d) means for switching between said outlet opening and said aperture and said port of said housing, to control the water to flow through said outlet opening of said housing and said nozzle and said cleaning member, said switching means including a valve member secured in said channel of said housing, said housing including an inlet communicating with said channel of said housing, said valve member including a first valve seat provided between said channel and said outlet opening of said housing, and including a second valve seat provided between said inlet and said port and said aperture of said housing, and means for selectively engaging with said first and said second valve seats.

13. The faucet coupling device according to claim 12, wherein said selectively engaging means includes a valve stem slidably engaged in said valve member and having two plugs secured thereto for selectively engaging with said first and said second valve seats.

14. A faucet coupling device for a faucet, said faucet coupling device comprising:
   a) a housing for attaching to the faucet and for receiving water from the faucet, said housing including a channel formed therein, and including a port and an aperture and an outlet opening formed therein and communicating with said channel thereof, b) a nozzle coupled to said aperture of said housing, c) a cleaning member coupled to said port of said housing, d) means for switching between said outlet opening and said aperture and said port of said housing, to control the water to flow through said outlet opening of said housing and said nozzle and said cleaning member, and e) a conduit secured to said aperture of said housing and communicating with said channel of said housing, a duct slidably engaged in said conduit and including an outer end extended outward of said conduit for securing to said nozzle.

15. The faucet coupling device according to claim 14, wherein said conduit includes a valve seat provided therein, said duct includes an inner end slidably received in said conduit and having a head for engaging with said valve seat of said conduit, and means for biasing said head to engage with and to block said valve seat of said conduit.

16. The faucet coupling device according to claim 14, wherein said duct includes a bore formed therein, and includes at least one orifice formed therein for communicating said bore of said duct with said conduit.

* * * * *